(12) United States Patent
Weng et al.

(10) Patent No.: US 7,423,404 B2
(45) Date of Patent: Sep. 9, 2008

(54) SAMPLE-LOADING SYSTEM AND ANTI-COLLISION DEVICE AND ANTI-COLLISION METHOD THEREOF

(75) Inventors: Yanwen Weng, Guangdong Province (CN); Jiankun Hu, Guangdong Province (CN); Xingcai Zhu, Guangdong Province (CN)

(73) Assignee: Shenzhen Mindray Bio-Medical Electronics Co, Ltd. (CN)

( * ) Notice: Subject to any disclaimer, the term of this patent is extended or adjusted under 35 U.S.C. 154(b) by 12 days.

(21) Appl. No.: 11/566,378

(22) Filed: Dec. 4, 2006

(65) Prior Publication Data

US 2008/0122396 A1 May 29, 2008

(30) Foreign Application Priority Data

Sep. 7, 2006 (CN) .................. 2006 1 0062502

(51) Int. Cl.
*G05B 1/06* (2006.01)
*G05B 11/01* (2006.01)
*G05B 19/29* (2006.01)

(52) U.S. Cl. .............. 318/640; 318/560; 318/567; 318/568; 318/569; 318/600

(58) Field of Classification Search ........ 318/560, 318/567, 568, 569, 600, 603, 638, 640
See application file for complete search history.

(56) References Cited

U.S. PATENT DOCUMENTS

| 3,657,627 | A | * | 4/1972 | Inaba et al. ............ 318/601 |
| 5,003,239 | A | | 3/1991 | Matthews et al. |
| 5,013,988 | A | * | 5/1991 | Sakano .................. 318/602 |
| 5,286,662 | A | | 2/1994 | Kuwata |
| 5,530,331 | A | * | 6/1996 | Hanei .................... 318/592 |
| 6,492,787 | B1 | * | 12/2002 | Hibino et al. ........ 318/568.11 |
| 6,723,287 | B1 | | 4/2004 | Ootatsume et al. |
| 6,747,429 | B2 | * | 6/2004 | Igarashi ................ 318/560 |
| 6,809,489 | B1 | * | 10/2004 | Yoshida et al. ......... 318/560 |

FOREIGN PATENT DOCUMENTS

| EP | 0 041 378 B1 | 11/1986 |
| JP | 2000-230841 | 8/2000 |

\* cited by examiner

*Primary Examiner*—Long Nguyen
*Assistant Examiner*—Thai T Dinh
(74) *Attorney, Agent, or Firm*—Vista IP Law Group LLP

(57) ABSTRACT

Some embodiments of the present invention provide an anti-collision device used for a sample-loading system. This device may include a code plate, an optical coupler, a location signal-detecting unit, a drive pulse counting unit and a drive pulse-sending unit. The optical coupler detects the code plate during the relative movement between the optical coupler and the code plate and outputs detection signals. The location signal detecting unit determines whether to output location signals to the drive pulse counting unit. The drive pulse counting unit judges whether collisions occur to the sample-loading system. Some embodiments of the present invention provide an anti-collision method and a sample-loading system comprising the anti-collision device.

20 Claims, 2 Drawing Sheets

SAMPLE-LOADING SYSTEM AND ANTI-COLLISION DEVICE AND ANTI-COLLISION METHOD THEREOF

RELATED APPLICATIONS

This application claims priority to Chinese Patent Application 200610062502.2, filed on Sep. 7, 2006, the contents of which are hereby incorporated by reference herein in its entirety.

BACKGROUND OF THE INVENTION

1. Field of the Invention

The present invention generally relates to sample-loading systems applied to the fields such as medical treatment, chemical industry etc. and, more particularly, to an anti-collision device and an anti-collision method thereof.

2. Discussion of the Related Art

Sample-loading systems are often used in medical treatment and chemical industry. Nowadays, the commonly adopted sample-loading systems are capable of automatically taking samples and loading the samples. In the process of movement (e.g., rotary movement or linear movement), the sample-loading system maybe collides with a person that is replacing a sample or a reagent, or collides with other objects. Also, a manipulative error maybe causes the sample-loading system to collide with other equipments. Either of the above-mentioned collisions can result in damages to the sample-loading system and errors in the test result. What is more serious is that the collision maybe causes injuries to the person. In order to ensure safeties of the person and apparatus, it is necessary to successfully detect the collisions occurring in the process of the movement of the sample-loading system. At present, for a rotary sample-loading system, the following three solutions are employed to detect the collisions occurred in the process of rotation.

The first solution is pressure detection. Specifically, a pressure sensor is placed at positions apt to be collided to detect changes of pressure value so as to judge whether the collision occurs. The shortcomings of the pressure detection are that the size of the drive portion is increased and the weight of the moving mechanism is also increased simultaneously. Moreover, the provision of the sensors also enhances the cost of the product (i.e., the sample-loading system with the sensors).

The second solution is acceleration detection. At the time when the sample-loading system is normally rotating, it has constant acceleration curves at stages of accelerating movement, uniform movement and decelerating movement. Through comparing the acceleration curve during rotating with that exhibited at normal working state, it is able to judge whether the collision occurs according to the curve difference therebetween. This solution needs to correctly distinguish the situation of a collision from that of a vibration generated when the sample-loading system accelerates at the start and decelerates at the end. Therefore, it is necessary to compare the signal detected by the acceleration sensor with a critical value via a signal-comparing unit and hereby judge the collisions under several kinds of conditions. Thus, the system has to be equipped with an accessorial signal-processing part, as a result of which its design is more complicated and inaccurate judgments tends to happen.

The third solution is driving pulse detection, whereby the collision is detected by detecting the waveform of a driving pulse. A rather significant difference exists between a pulse signal in case of a normal running drive motor and that of a collided drive motor, so it is possible to judge whether the collision occurs via detecting any difference of the pulse signal from that of a normal running drive motor. Similar to the acceleration detection, this solution also demands an accessorial signal-processing part, and the design thereof is rather complicated.

SUMMARY OF THE INVENTION

An object of the present invention is to provide an anti-collision device used for a sample-loading system, and an anti-collision method, both of which use a low-cost design to effectively prevent the sample-loading system from colliding with other objects in the process of movement.

The present invention realizes the above object by providing an anti-collision device used for a sample-loading system. The sample-loading system includes a moving mechanism and a drive motor arranged for driving the moving mechanism. The anti-collision device includes a code plate, an optical coupler, a location signal detecting unit, a drive pulse counting unit and a drive pulse sending unit. The code plate defines a number of equidistant light penetrating gaps. The optical coupler is configured for detecting relative location change of the code plate. Either the code plate or the optical coupler connects to and moves along with the moving mechanism. The optical coupler, the location signal detecting unit, the drive pulse counting unit, the drive pulse sending unit and the drive motor are electrically connected in series. The optical coupler detects the light penetrating gaps of the code plate during the relative movement between the optical coupler and the code plate and outputs detection signals indicative of periodically-changed electrical levels. The location signal detecting unit receives the detection signals and determines whether to output location signals to the drive pulse counting unit according to the detection signals. The drive pulse counting unit is configured for resetting the drive pulse counting unit when receiving the location signals, and for judging whether the counted number of the drive pulse is equal to or greater than a setvalue when not receiving the location signals. If yes, the drive pulse counting unit controls the drive pulse sending unit to stop sending the drive pulse to the drive motor and resets the drive pulse counting unit. If "no", the drive pulse counting unit controls the drive pulse sending unit to send one drive pulse to the drive motor and add 1 to the counted number of the drive pulse.

Further, the light penetrating gaps are strip-shaped holes or circular holes defined at the periphery of the code plate.

Further, the moving mechanism is a rotation mechanism having a rotation axle. The code plate is a circular disk, which fixedly hitches the rotation axle and coaxially rotates therewith. The optical coupler is orientated so that the light penetrating gaps moves to a detecting place of the optical coupler.

Alternatively, the moving mechanism is a linearly moving mechanism. The optical coupler is fixed on the moving mechanism. The code plate is a rectangle disk and is orientated so that the light penetrating gaps moves to a detecting place of the optical coupler.

Further, the location signal corresponds to an electrical level jump in the detection signal or to the cycle of an output signal in the detection signal.

The present invention realizes the above object by further providing an anti-collision method used for a sample-loading system. The sample-loading system includes an indicator plate, a detector and a moving mechanism. Either the indicator plate or the detector moves along with the moving mechanism. The method includes the following steps of: (A1) the detector detecting indicator points of the indicator plate during the relative movement between the detector and the indicator plate and outputting detection signals indicative of periodically-changed electrical levels; (B1) a location signal detecting unit receiving the detection signals and determining whether to output location signals to a drive pulse counting unit; (C1) the drive pulse counting unit receiving the location signals, and then step D1 if the location signals are received, or then step E1 if the location signals are not received; (D1) resetting the drive pulse counting unit; (E1) judging whether the counted number of the drive pulse is equal to or greater than a set value, and then step F1 if the judged result is "yes", or then step G1 if "no"; (F1) controlling a drive pulse sending unit to stop sending the drive pulse to a drive motor and resetting the drive pulse counting unit; and (G1) controlling the drive pulse sending unit to send one drive pulse to the drive motor and add 1 to the counted number of the drive pulse.

The indicator plate referred to is similar to the code plate, except that the indicator points can be any one selected from the group consisting of light penetrating gaps, micro mirrors or point light sources which are all uniformly distributed on the indicator plate. The detector is a light-signal transmitting and/or receiving device.

Further to Step B1, the location signal detecting unit outputs the location signals when it detects the electrical level jump of the detection signals or when it detects a rising-edge or a descending-edge of the detection signals. Subsequent to D1, the drive pulse counting unit controls the drive pulse sending unit to send one drive pulse to the drive motor. Further to step F1, the drive pulse sending unit gives an alarm after it stops sending the drive pulse.

The present invention realizes the above object by further providing a sample-loading system with an anti-collision function, which includes a probe, a moving mechanism configured for driving the probe to move and a drive motor configured for driving the moving mechanism. The sample-loading system further includes a location signal generating unit, a location signal detecting unit, a drive pulse counting unit and a drive pulse sending unit, which are electrically connected in series. The location signal generating unit outputs detection signals indicative of periodically-changed electrical levels according to the movement of the moving mechanism. The location signal detecting unit receives the detection signals and determines whether to output location signals to the drive pulse counting unit according to the detection signals. The drive pulse counting unit is configured for resetting the drive pulse counting unit when receiving the location signals and judging whether the counted number of the drive pulse is equal to or greater than a set value when not receiving the location signals. If the judged result is "yes", the drive pulse counting unit controls the drive pulse sending unit to stop sending the drive pulse to the drive motor and reset the drive pulse counting unit. If "no", the drive pulse counting unit controls the drive pulse sending unit to send one drive pulse to the drive motor and add 1 to the counting number of the drive pulse.

The location signal generating unit mentioned above includes a Hall position sensor.

Further, the location signal generating unit can includes an indicator plate having indicator points, and a detector useful for detecting relative location change of the indicator plate. Either the indicator plate or the detector connects to and moves along with the moving mechanism. The detector detects indicator points of the indicator plate during the relative movement between the detector and the indicator plate and outputs detection signals indicative of periodically-changed electrical levels.

According to the present invention, whether a collision occurs during the movement of the sample-loading system is found out through location detection. Specifically, the rotating process of the sample-loading system is fractionalized into a number of phases, and the sample-loading system continuously and sequentially moves to an appointed location during the whole movement process. Every time the sample-loading system moves to the next location from the present location, the drive motor needs to rotate for certain steps designed by the system. Beginning from the present location, if the drive motor has rotated for the designed steps, while the sample-loading system doesn't arrive to the next location yet, it shows that the sample-loading system encounters collisions and the system whereupon stops working and gives an alarm. Thus, the personal safety is ensured and the apparatus is protected from being damaged. As compared with the prior art, the present invention achieves the following advantageous effect. 1) The mechanical structure is simple. The present invention only necessitates a code plate, a detecting optical coupler and corresponding circuits, either the code plate or the optical coupler fixed, the other movable along with the moving mechanism. Thereby, a relative movement exists between the code plate and the optical coupler, whereby the location detection is achievable using the optical coupler to detect the light penetrating gaps of the code plate. As seen from this, the size of the sample-loading system is not increased, which is helpful to miniaturize the sample-loading system. 2) The processing circuit is simple, which only demands the acquisition of the optical coupler signal. 3) The detecting process is easily achievable. 4) Acceleration and deceleration have no effect on the present invention which is associated with location only, so inaccurate judgments will not occur. 5) High detecting sensitivity is achieved.

Other and further objects of the invention will be apparent from the following drawings and description of preferred embodiments of the invention in which like reference numerals are used to indicate like parts in the various views.

BRIEF DESCRIPTION OF THE DRAWINGS

Many aspects of the present invention can be better understood with reference to the following drawings. The components in the drawings are not necessarily drawn to scale, the emphasis instead being placed upon clearly illustrating the principles of the present invention. Moreover, in the drawings, like reference numerals designate corresponding parts throughout the several views.

DESCRIPTION OF THE PREFERRED EMBODIMENTS

Reference will now be made to the figures to describe the present invention in detail.

Figure 1:
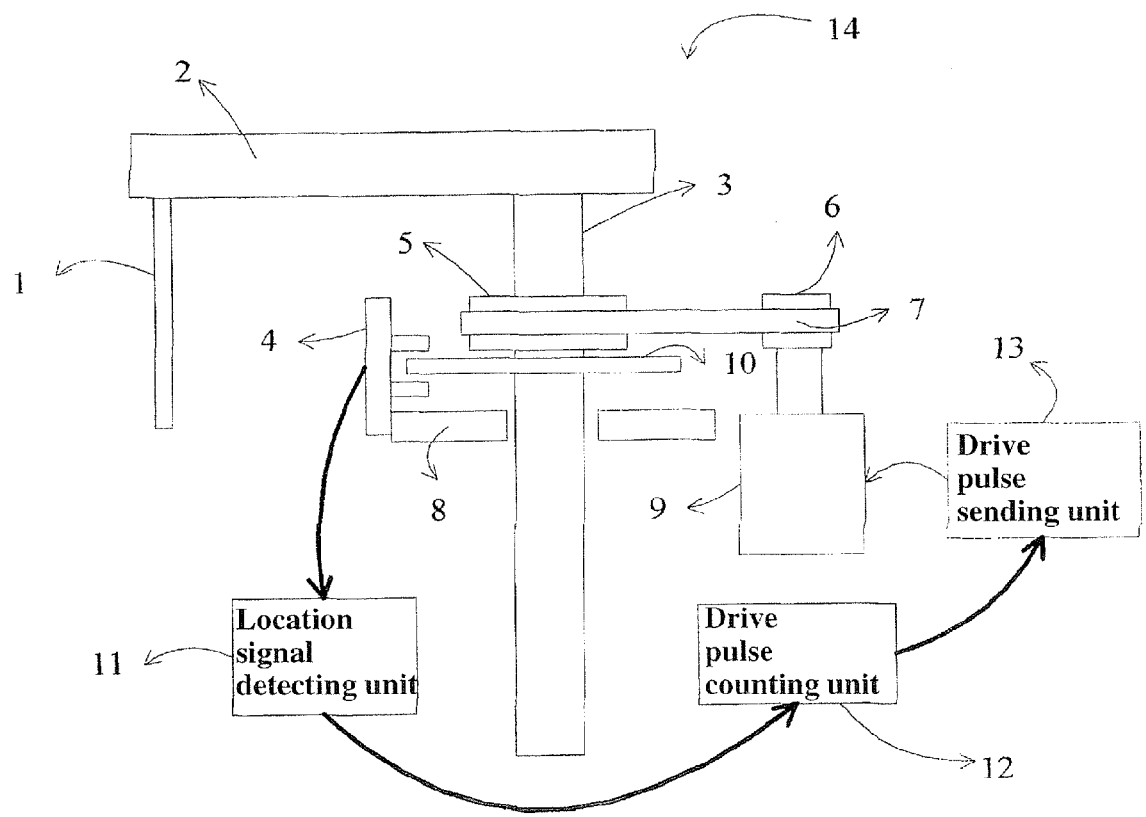
FIG. 1 is a holistic, structural view of a sample-loading system in accordance with the preferred embodiment of the present invention.
Figure 2:
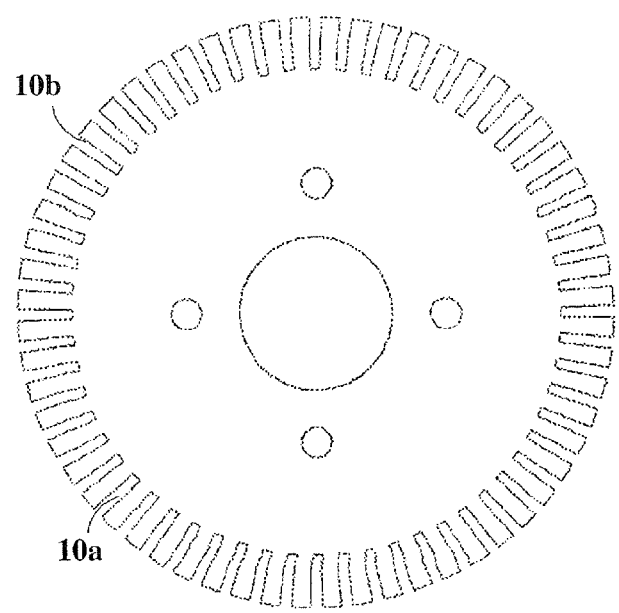
FIG. 2 is a structural view of a code plate in accordance with the preferred embodiment of the present invention.

Referring to FIG. 1, a rotation-mode sample-loading system 14 in accordance with the first preferred embodiment of the present invention is shown. In this embodiment, the moving mechanism is a rotation axle 3. A drive motor 9 connects to a small belt wheel 6 and drives it to rotate. The small belt wheel 6 connects to a large belt wheel 5 via a synchronous belt 7 and transfers a rotation movement thereto. The large belt wheel 5 drives the rotation axle 3 and a code plate 10 to synchronously move (i.e., to rotate). A probe 1 connects to a rocking arm 2 and is rotated to an appointed position by the rocking arm 2 driven by the rotation axle 3 connected thereto. The code plate 10 is a circular disk and defines a number of equidistant gaps 10a at the periphery thereof, which gaps can be strip-shaped or dentate holes, or alternatively circular holes as shown in FIG. 2. The code plate 10 fixedly hitches the rotation axle 3 and coaxially rotates therewith. An optical coupler 8, immovably installed on a bracket 4 (i.e., the optical coupler 8 doesn't rotate along with the rotation axle 3 during working) is orientated so that the gaps 10a moves to the detecting place of the optical coupler 8. The optical coupler 8 detects the code plate 10 and hereby obtains a location signal of the code plate 10, which signal is then sent to a drive pulse counting unit 12 through a location signal detecting unit 11. The drive pulse counting unit 12 thus judges whether a collision occurs to the sample-loading system 14 according to the location signal and controls a drive pulse sending unit 13 in a way to or not to send a pulse signal to the drive motor 9.

As an alternative to a rotation-mode sample-loading system, the optical coupler can also be fixed to the rotation axle and rotate therewith, while the code plate is immovably fixed in relation to the rotation axle (i.e., the code plate doesn't rotate along with the rotation axle during working).

With this location detecting method, it demands to fractionalize the rotating process into a number of phases and thereby defines a number of location points while without any interference to the normal operations of the sample-loading system, in order for judging whether the collision occurs. In the first embodiment, the code plate 10 is used for fractionalizing the rotating process, and the optical coupler 8 for obtaining the location signal. The code plate 10 is sized according to its mechanical structure, and the specific amounts to be fractionalized into is codetermined by the size of the code plate 10, an effective detecting size of the optical coupler 8, an anti-collision sensitivity of the system, transmission ratio, and so on. For example, as shown in FIG. 2, the code plate 10 is fractionalized into n portions, and there are totaling 2n tooth edges 10b each confirming a location. When a tooth edge 10b traverses the optical coupler 8, the output electrical level of the optical coupler 8 jumps. The location signal detecting unit 11 detects the signal indicative of the jumped electrical level of the optical coupler 8 and regards it as the location signal. When the signal indicative of the jumped electrical level of the optical coupler 8 is detected, it denotes that the sample-loading system rotates to the location corresponding to the tooth edge 10b. When this signal is detected once again, it denotes that the sample-loading system rotates to the location corresponding to the next tooth edge 10b. Thus, the width of and the space between the gaps 10a of the code plate 10 can be so designed that the rotation movement of the sample-loading system can be fractionalized into 2n portions. Because it is possible to detect the collision state in the process of rotation based on the 2n location points, the anti-collision purpose is achievable thereby. Of course, the code plate having different structures (e.g., a code plate with circular gaps) can achieve the same purpose.

With the location detection realized, it is to determine whether collisions occur to the sample-loading system according to the location signal as detected. The configuration of the system is such that the drive motor 9 has to rotate a fixed number of steps for example m steps to move from the current location to the next one (i.e., the drive pulse sending unit 13 sends m drive pulses to the drive motor 9). If the drive motor 9 rotates more than m steps, whereas the location signal detecting unit still doesn't detect any signal indicative of a jumped electrical level of the optical coupler 8, it shows that the sample-loading system doesn't arrive at the next location yet. The only reason therefor is that the sample-loading system is hindered and fails to move to the desired location in the process of rotation. Thereby, occurrences of collision can be judged.

Figure 3:
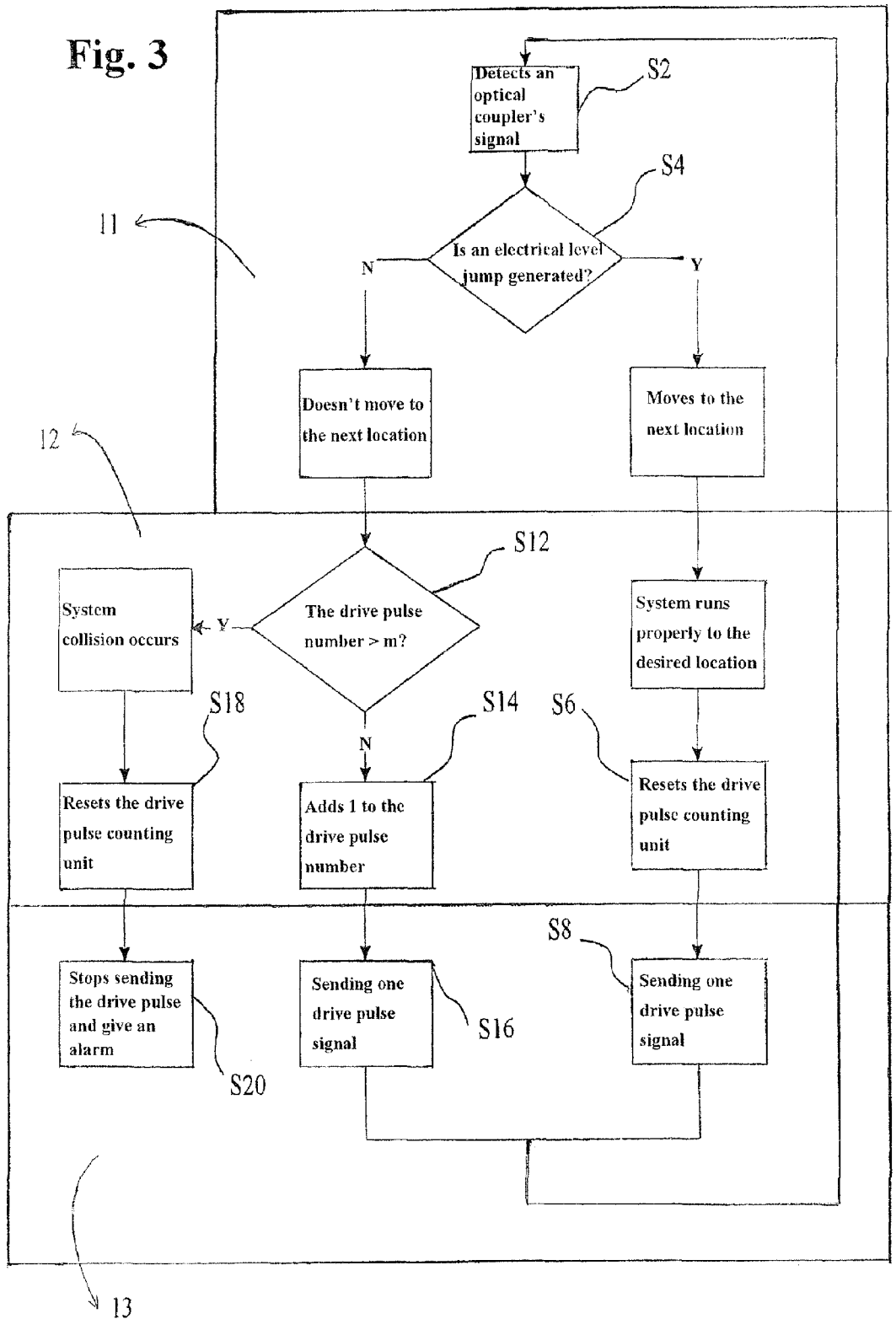
FIG. 3 is a flow chart of an anti-collision detection process in accordance with the preferred embodiment of the present invention.

A detailed detecting process is shown in FIG. 3. Location detection needs to be performed every time before a drive pulse is sent, so that the collision can be timely found. Therefore, step S2 is performed firstly to detect the output signal of the optical coupler 8 through the location signal detecting unit 11. The following step S4 is performed to judge whether the signal of the optical coupler 8 generates an electrical level jump. If the output electrical level jumps, it denotes that the sample-loading system rotates to a location corresponding to certain tooth edge, and then step S6 is performed. If the electrical level doesn't jump, it denotes that the sample-loading system doesn't rotate to the location corresponding to that tooth edge but remains between two tooth edges, and then step S12 starts. The location signal detecting unit 11 sends the result to the drive pulse counting unit 12 which takes corresponding measures according to different results. At step S12 which happens where the sample-loading system doesn't rotate to the location corresponding to the tooth edge, the drive pulse counting unit detects whether the number of the drive pulse as counted is larger than m, a value set in advance for the system. If yes, collisions have occurred. Step S18 is then performed to reset the drive pulse counting unit, and step S20 is sequentially performed to inform the drive pulse sending unit to stop sending the drive pulse and give an alarm. If no, it denotes that the sample-loading system doesn't rotate to the desired location, and that drive pulse needs to be sequentially sent. Step S14 is then initiated to add 1 to the number of the drive pulse as counted, and finally step S16 is carried out to inform the drive pulse sending unit to send one drive pulse signal. If the output electrical level of the optical coupler 8 jumps (i.e., the sample-loading system rotates to the location corresponding to certain tooth edge), it denotes that the system is running properly. In this case, step S6 is performed to reset the drive pulse counting unit so that counting is restarted. Finally, step S8 is on to inform the drive pulse sending unit 13 to send one drive pulse signal. Here, one process of sending drive pulse is accomplished. If a next drive pulse needs to be sent, the judgment as to location detection should be restarted from the very beginning.

In the above-mentioned process, steps S2, S4 are processed by the location signal detecting unit 11, steps S6, S12, S14, S18 by the drive pulse counting unit 12, and steps S8, S16, S20 by the drive pulse sending unit 13.

From the above-mentioned detecting process, it can be seen that the preset value m for the system directly affects the sensitivity of anti-collision detection. The value m is determined by that to what extend the whole rotating process is fractionalized.

According to the present invention, the location signal can be output by the location signal detecting unit when the electrical level jump in the output signal of the optical coupler is detected. The location signal can also be output by the location signal detecting unit according to the cycle of the signal output by the optical coupler. Specifically, the location signal is output when the location signal detecting unit detects a rising-edge or a descending-edge of the output signal of the optical coupler.

According to the second preferred embodiment, the present invention is adapted for use in a linear-movementmode sample-loading system. In this embodiment, the moving mechanism is a linearly moving mechanism. Preferably, the optical coupler is fixed on and moves with the moving mechanism. The code plate is a rectangle disk that is fixed on the moving track of the moving mechanism, and doesn't move in relation to the moving mechanism. In addition, the code plate has one edge parallel with the moving track of the moving mechanism so that the gaps of the code plate moves to the detecting place of the optical coupler. The location signal detecting unit, the drive pulse counting unit, and the drive pulse sending unit of the second embodiment may be identical to those of the first embodiment, and have the same anti-collision function as well.

It is to be noted that above-mentioned code plate with gaps are replaceable with an indicator plate with uniformly distributed micro mirrors or point light sources. At the same time an appropriate light-signal transmitting and/or receiving detector is used for detecting the light-signal change caused by relative movement between the indicator plate and the detector. Specifically, in case of micro mirrors, the detector detects the location change of the indicator plate according to the light reflected by the micro mirrors. While in case of point light sources, the detector detects the location change of the indicator plate according to the detected light from the point light sources. Then the detector generates detected signal that can be used for operations similar to those concerning the location signal detecting unit, drive pulse counting unit, and drive pulse sending unit of the first embodiment as mentioned above.

In addition, a Hall position sensor can be used for replacing the above-mentioned optical coupler and other location-change detecting means. Hall position sensor and Hall theory are known to the person skilled in the art, so they are not described in greater detail herein.

All in all, the present invention can effectively detect the collision states of a sample-loading system and timely respond to stop the operations of the sample-loading system, so that the personal safety is ensured and the apparatus is protected from being damaged. The probe is particularly well protected Linder the present invention, and therefore has a prolonged life.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

The invention claimed is:

1. An anti-collision device for a sample-loading system, the sample-loading system comprising a moving mechanism and a drive motor configured for driving the moving mechanism, the anti-collision device comprising;
   a code plate defining a plurality of equidistant light penetrating gaps;
   an optical coupler configured to detect relative location change of the code plate, either the code plate or the optical coupler connecting to and moving along with the moving mechanism;
   a location signal detecting unit, a drive pulse counting unit and a drive pulse-sending unit, which units together with the drive motor are electrically connected in series;
   wherein the optical coupler detects the light penetrating gaps of the code plate during a relative movement between the optical coupler and the code plate and outputs detection signals indicative of periodically-changed electrical levels; the location signal detecting unit receives the detection signals and determines whether to output location signals to the drive pulse counting unit according to the detection signals; the drive pulse counting unit is configured for resetting the drive pulse counting unit when receiving the location signals and judging whether a counted number of a drive pulse is equal to or greater than a set value when not receiving the location signals; and if a judged result is "yes", the drive pulse counting unit controls the drive pulse sending unit to stop sending the drive pulse to the drive motor and reset the drive pulse counting unit, if "no", the drive pulse counting unit controls the drive pulse sending unit to send one drive pulse to the drive motor and add one to the counting number of the drive pulse.

2. The anti-collision device as claimed in claim 1, wherein the light penetrating gaps comprise strip-shaped holes or circular holes defined at a periphery of the code plate.

3. The anti-collision device as claimed in claim 2, wherein the moving mechanism is comprises a rotation mechanism having a rotation axle, the code plate comprises a circular disk fixedly hitching the rotation axle and coaxially rotating along with the rotation axle, and the optical coupler is orientated so that the light penetrating gaps move to a detecting place of the optical coupler.

4. The anti-collision device as claimed in claim 2, wherein the moving mechanism comprises a linearly moving mechanism, the optical coupler is fixed on the moving mechanism, and the code plate comprises a rectangular disk being orientated so that the light penetrating gaps move to a detecting place of the optical coupler.

5. The anti-collision device as claimed in claim 4, wherein the location signals correspond to an electrical level jump in the detection signals or a cycle of an output signal in the detection signal.

6. An anti-collision method for a sample-loading system, wherein the sample-loading system comprises an indicator plate, a detector, and a moving mechanism, and wherein either the indicator plate or the detector move along with the moving mechanism, the method comprising:
   (A1) the detector detecting indicator points of the indicator plate during a relative movement between the detector and the indicator plate and outputting detection signals indicative of periodically-changed electrical levels;
   (B1) a location signal-detecting unit receiving the detection signals and determining whether to output location signals to a drive pulse counting unit according to the detection signals;
   (C1) the drive pulse counting unit receiving the location signals, and then action D1 if the location signals are received, or then action E1 if the location signals are not received;
   (D1) resetting the drive pulse counting unit;
   (E1) judging whether a counted number of drive pulse is equal to or greater than a set value, and then action F1 if a judged result is "yes", or then action G1 if "no";
   (F1) controlling a drive pulse sending unit to stop sending the drive pulse to a drive motor and resetting the drive pulse counting unit; and
   (G1) controlling the drive pulse sending unit to send one drive pulse to the drive motor and add one to the counted number of the drive pulse.

7. The anti-collision method as claimed in claim 6, wherein the indicator points comprise light penetrating gaps uniformly distributed on the indicator plate.

8. The anti-collision method as claimed in claim 6, wherein the indicator points comprises micro mirrors or point light sources uniformly distributed on the indicator plate.

9. The anti-collision method as claimed in claim 6, wherein the detector comprises a light-signal transmitting and/or receiving device.

10. The anti-collision method as claimed in claim 7, wherein the location signal detecting unit outputs the location signals when it detects an electrical level jump of the detection signals or when it detects a rising-edge or a descending-edge of the detection signals in the action B1.

11. The anti-collision method as claimed in claim 10, wherein the drive pulse counting unit controls the drive pulse sending unit to send one drive pulse to the drive motor after the action D1.

12. The anti-collision method as claimed in claim 11, wherein the drive pulse-sending unit gives an alarm after it stops sending the drive pulse in the action F1.

13. A sample-loading system with an anti-collision function, comprising: a probe, a moving mechanism configured to drive the probe to move, a drive motor configured to drive the moving mechanism, the sample-loading system further comprising:
    a location signal generating unit, a location signal detecting unit, a drive pulse counting unit and a drive pulse sending unit, which units together with the drive motor are electrically connected in series;
    wherein the location signal generating unit outputs detection signals indicative of periodically-changed electrical levels according to a movement of the moving mechanism, the location signal detecting unit receives the detection signals and determines whether to output location signals to the drive pulse counting unit according to the detection signals; the drive pulse counting unit is configured for resetting the drive pulse counting unit when receiving the location signals and judging whether the counted number of drive pulse is equal to or greater than a set value when not receiving the location signals; and if a judged result is "yes", the drive pulse counting unit controls the drive pulse sending unit to stop sending the drive pulse to the drive motor and reset the drive pulse counting unit, if "no", the drive pulse counting unit controls the drive pulse sending unit to send one drive pulse to the drive motor and add one to the counted number of the drive pulse.

14. The sample-loading system as claimed in claim 13, wherein the location signal-generating unit comprises a Hall position sensor.

15. The sample-loading system as claimed in claim 13, wherein the location signal-generating unit comprises:
    an indicator plate comprising indicator points; and
    a detector configured to detect relative location change of the indicator plate, either the indicator plate or the detector connecting to and moving along with the moving mechanism, the detector further configured to detect indicator points of the indicator plate during a relative movement between the detector and the indicator plate and outputting detection signals indicative of periodically-changed electrical levels.

16. The sample-loading system as claimed in claim 15, wherein the indicator points comprise light penetrating gaps uniformly distributed on the indicator plate.

17. The sample-loading system as claimed in claim 15, wherein the indicator points comprise micro mirrors or point light sources uniformly distributed on the indicator plate.

18. The sample-loading system as claimed in claim 15, wherein the detector comprises a light-signal transmitting and/or receiving device.

19. The sample-loading system as claimed in claim 16, wherein the moving mechanism is a rotation mechanism comprising a rotation axle, the indicator plate comprises a circular disk, fixedly hitching the rotation axle and coaxially rotating along with the rotation axle, and the detector is orientated so that the light penetrating gaps move to a detecting place of the detector.

20. The sample-loading system as claimed in claim 16, wherein the moving mechanism comprises a linearly moving mechanism, the detector is fixed on the moving mechanism, and the indicator plate is a rectangular disk which is orientated so that the light penetrating gaps move to a detecting place of the detector.

* * * * *